United States Patent
Lyons et al.

(10) Patent No.: US 6,933,289 B2
(45) Date of Patent: Aug. 23, 2005

(54) INHIBITION OF IRRITATING SIDE EFFECTS ASSOCIATED WITH USE OF A TOPICAL OPHTHALMIC MEDICATION

(75) Inventors: Robert T. Lyons, Laguna Hills, CA (US); James N. Chang, Newport Beach, CA (US)

(73) Assignee: Allergan, Inc., Irvine, CA (US)

(*) Notice: Subject to any disclaimer, the term of this patent is extended or adjusted under 35 U.S.C. 154(b) by 127 days.

(21) Appl. No.: 10/613,097

(22) Filed: Jul. 1, 2003

(65) Prior Publication Data

US 2005/0004074 A1 Jan. 6, 2005

(51) Int. Cl.[7] ........................ A61K 31/715; A61K 9/14; C07C 59/00; C07C 59/147; C07C 59/185
(52) U.S. Cl. ........................ 514/58; 554/214; 554/117; 514/530; 514/772.4; 424/488
(58) Field of Search ........................ 514/58, 530, 772.4; 554/214, 117; 424/488; 536/1.11; 523/103

(56) References Cited

U.S. PATENT DOCUMENTS

| | | | |
|---|---|---|---|
| 4,470,965 A | 9/1984 | Wolf et al. | |
| 4,727,064 A | 2/1988 | Pitha | |
| 5,419,898 A | 5/1995 | Ikejiri et al. | |
| 5,422,116 A | 6/1995 | Yen et al. | |
| 5,472,954 A | 12/1995 | Loftsson | |
| 5,494,901 A | 2/1996 | Javitt et al. | |
| 5,558,876 A | 9/1996 | Desai et al. | |
| 5,688,819 A | 11/1997 | Woodward et al. | |
| 5,891,913 A | 4/1999 | Sallmann et al. | |
| 6,107,343 A | 8/2000 | Sallmann et al. | |
| 6,232,343 B1 * | 5/2001 | Ikari et al. | 514/530 |
| 6,407,079 B1 | 6/2002 | Muller et al. | |
| 6,420,407 B1 | 7/2002 | Horn | |
| 6,455,547 B1 | 9/2002 | Kis | |
| 6,468,548 B1 | 10/2002 | Kis | |
| 6,479,556 B2 | 11/2002 | Doi et al. | |
| 6,562,873 B2 * | 5/2003 | Olejnik et al. | 514/772.4 |

(Continued)

FOREIGN PATENT DOCUMENTS

| | | |
|---|---|---|
| EP | 0435682 A3 | 12/1990 |
| EP | 0435682 A2 | 12/1990 |
| EP | 0579435 A1 | 7/1993 |
| WO | WO 94/12217 | 6/1994 |
| WO | WO 95/00144 | 1/1995 |

OTHER PUBLICATIONS

Martin et al., Physical Pharmacy: Physical and Chemical Principles in the Pharmaceutical Sciences., 1993., Lea & Febiger., Fourth Edition., pp. 259–260.*

(Continued)

*Primary Examiner*—James O. Wilson
*Assistant Examiner*—Matthew L. Fedowitz
(74) *Attorney, Agent, or Firm*—Brent A. Johnson; Robert J. Baran; Martin A. Voet

(57) ABSTRACT

This invention relates to a method of reducing an irritating or adverse side effect associated with the topical use of an active ophthalmic drug comprising incorporating an effective amount of a cyclodextrin or cyclodextrin derivative into a formulation to complex the active drug such that the concentration of the free active drug is reduced below a tolerable threshold, and incorporating an effective amount of a viscosity increasing agent in said formulation such that the bioavailability of said drug is high enough to be therapeutically effective, wherein the cyclodextrin or cyclodextrin derivative is not required to solubilize the active drug.

Figure 1:
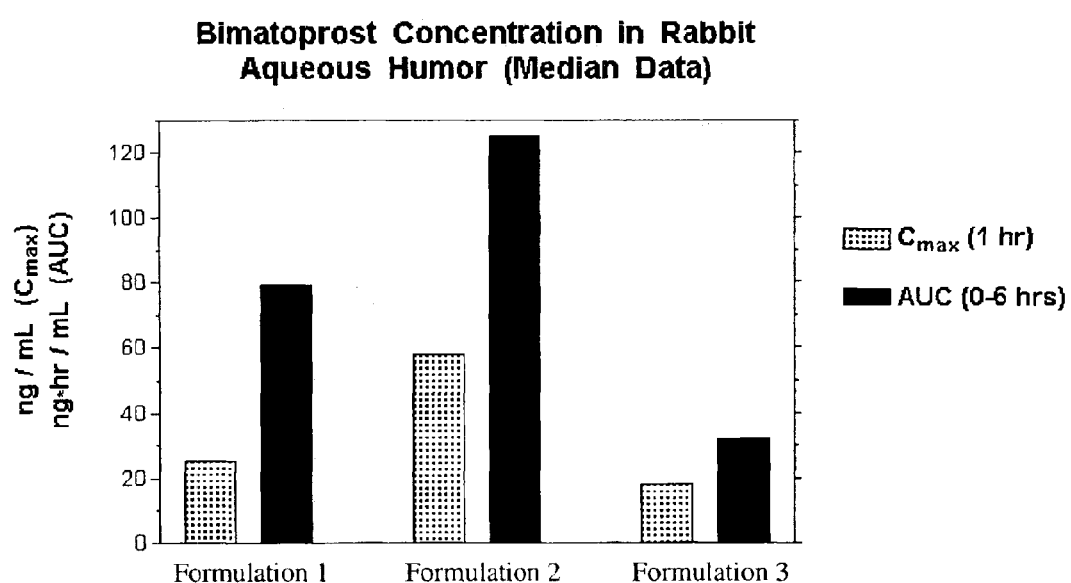

Another aspect of this invention relates to topical ophthalmic formulations comprising an active drug, a cyclodextrin or cyclodextrin derivative, and a viscosity-enhancing agent, in effective amounts as stated above.

14 Claims, 1 Drawing Sheet

U.S. PATENT DOCUMENTS

| | | | |
|---|---|---|---|
| 6,646,001 B2 * | 11/2003 | Hellberg et al. | 514/530 |
| 6,828,356 B2 * | 12/2004 | Su et al. | 523/105 |
| 2002/0035264 A1 * | 3/2002 | Kararli et al. | 546/300 |
| 2003/0232089 A1 * | 12/2003 | Singh et al. | 424/488 |

OTHER PUBLICATIONS

U.S. Pharmacopeia., 2004 USP Dictionary of USAN and International Drug Names., pp. 119–120.*

Gennaro et al.., Remington: The Science and Practice of Pharmacy., 1995., Lippincott Williams & Wilkins., Nineteenth Edition., pp. 173–178.*

Bito, L.Z. *Biological Protection with Prostaglandins*, Cohen, M.M., ed., Boca Raton, FL, CRC Press Inc., 1985, pp 231–252.

Bito, L.Z., *Applied Pharmacology in the Medical Treatment of Glaucomas*, Drance, S.M. and Neufeld, A.H., eds., New York, Grune & Stratton, 1984, pp 477–505.

Bowen, John M. et al., *Identification of Cocaine and Phencyclidine by Solute–Induced Circular Dichroism*; Analytical Chemistry, vol. 53, No. 14, Dec. 1981, pp 2239–2242.

Han, Soon M. et al., Solute–Induced Circular Dichroism: Complexation of Achiral Drugs with Cyclodextrin; Analytical Chemistry, vol. 56, No. 14, Dec. 1984, pp 2822–2825.

* cited by examiner

INHIBITION OF IRRITATING SIDE EFFECTS ASSOCIATED WITH USE OF A TOPICAL OPHTHALMIC MEDICATION

FIELD OF THE INVENTION

The present invention relates to pharmaceutical compositions. In particular, the present invention relates to topical ophthalmic compositions containing an active drug.

BACKGROUND OF THE INVENTION

1. Description of Related Art

Active drugs often have undesirable side effects at their therapeutically effective concentrations. This is particularly problematic for topical use in sensitive areas such as the eyes, where irritation is very difficult to avoid even for relatively mild drugs. As a result, formulating topical ophthalmic drugs is a particularly challenging problem. This is unfortunate because topical ophthalmic use of drugs has been found to be very useful in managing many conditions affecting the eye such as dry eye, infection, inflammation, allergy, and glaucoma. Glaucoma is a particularly devastating disease of the eye characterized by increased intraocular pressure, which is often treated by topical ophthalmic application of a drug. Glaucoma occurs in about 2% of all persons over the age of 40 and may be asymptotic for years before progressing to rapid loss of vision. In cases where surgery is not indicated, many drugs have been found to be useful in treating glaucoma by topical application including β-adrenoreceptor antagonists and α$_2$-adrenoreceptor agonists. Recently, prostaglandins have been shown to be particularly useful in the topical treatment of glaucoma.

Whereas prostaglandins appear to be devoid of significant intraocular side effects, ocular surface (conjunctival) hyperemia, foreign-body sensation, and itching (pruritus) have been consistently associated with the topical ocular use of such compounds, in particular PGF$_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

U.S. Pat. No. 5,688,819, commonly assigned to Allergan, Inc., and incorporated herein by reference discloses that derivatives prostaglandins known as prostamides, wherein the carboxylic acid group is replaced by an amide substituent have pronounced effects on smooth muscle and are potent ocular hypotensive agents. Additionally, prostamides cause significantly lower ocular surface hyperemia than the parent compounds. One prostamide exemplary of the these effects is bimatoprost, which is marketed by Allergan, Inc. under the trade name Lumigan®, which has the structure shown in Formula I below.

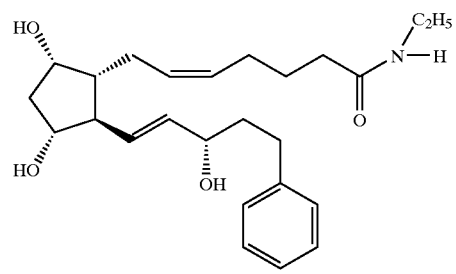

Formula I

However, although bimatoprost is associated with significantly less hyperemia and other irritating side effects compared to certain prostaglandins, further improvement is still highly desirable.

Cyclodextrins are cyclic oligosaccharides containing 6, 7, or 8 glucopyranose units, referred to as α-cyclodextrin (structure depicted below), β-pharmaceutical or γ-cyclodextrin respectively, which are often used in pharmaceutical formulations.

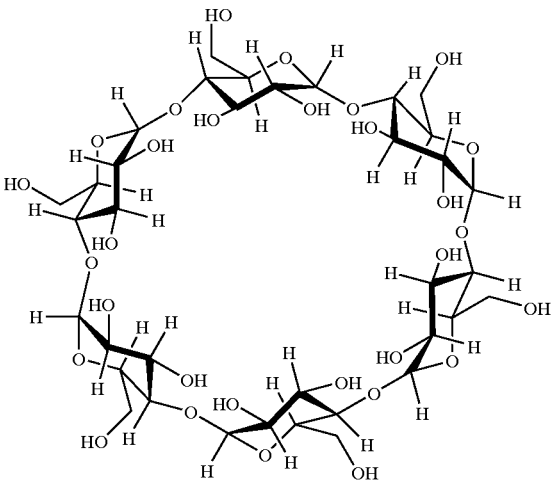

α-CYCLODEXTRIN

Cyclodextrins have a hydrophilic exterior, which makes them water soluble, and a hydrophobic interior which forms a cavity. In an aqueous environment, hydrophobic portions of molecules often enter the hydrophobic cavity of cyclodextrin to form inclusion compounds. Although inclusion compounds are often formed between cyclodextrins and hydrophobic molecules, cyclodextrins are also capable of other types of noncovalent (nonbonding) interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. One or more of these hydroxyl groups can be reacted with any of a number of reagents to form a large variety of cyclodextrin derivatives. Some of the more common derivatives of cyclodextrin are hydroxypropyl ethers, sulfonates, and sulfoalkylethers.

In pharmaceutical formulations, cyclodextrins and cyclodextrin derivatives are often used to improve the solubility of an active drug. In many cases, it is believed that inclusion compounds formed between a cyclodextrin or cyclodextrin derivative and a lipophilic drug are important to the enhanced solubility observed. The lipophilic portion of the drug is enclosed in the cyclodextrin cavity forming favorable hydrophobic interactions with the inside of the cavity, and also reducing or eliminating the unfavorable interactions between water and the hydrophilic interior of the cavity and water and the hydrophobic drug. While inclusion compounds are involved in many cases of enhanced solubility, other interactions between cyclodextrins and insoluble compounds can also improve solubility. As mentioned, the use of cyclodextrins in pharmaceutical compositions is well known in the art. For example, U.S. Pat. No. 6,407,079 teaches the use of cyclodextrin derivatives to form inclusion compounds that improve the solubility of the active drug. EP 579435 teaches the use of cyclodextrin or a cyclodextrin derivative and a water soluble polymer to solubilize or stabilize an active drug. The use of cyclodextrin and cyclodextrin derivatives in ophthalmic formulations is also well known. For example, European Patent Application 0435682 A2 teaches the use of cyclodextrins in ophthalmic compositions with prostaglandins to treat ocular hypertension. Generally, these complexes are formed in such a way that the formulation is saturated with the active drug. For example, the mixture is heated to dissolve, cooled, and the remaining solid drug removed via centrifugation or filtration. However, it is not taught in the art that the use of cyclodextrin or cyclodextrin derivatives at concentrations significantly beyond that needed to solubilize or stabilize the active drug should have additional benefits. Rather, one would expect that increasing the amount of cyclodextrin in the formulation beyond that required to solubilize the drug would increase the amount of drug complexed to the cyclodextrin, which might significantly impair the bioavailability of the drug, reducing the effectiveness of the formulation.

SUMMARY OF THE INVENTION

We have surprisingly discovered that although the complexation of an active drug with a cyclodextrin or cyclodextrin derivative does reduce the bioavailability of the drug, this loss can be countered by carefully optimizing the cyclodextrin/active drug molar ratio and by using a viscosity-enhancing agent. As such, this invention relates to a method of reducing an irritating or adverse side effect associated with the topical ophthalmic use of an active ophthalmic drug. This is accomplished by taking advantage of the synergistic benefits of the combined use of a cyclodextrin or cyclodextrin derivative in optimum molar ratio with said active drug and a viscosity-enhancing agent.

One aspect of this invention relates to a method of reducing an irritating or adverse side effect associated with the topical ophthalmic use of an active ophthalmic drug comprising incorporating an effective amount of a cyclodextrin or cyclodextrin derivative into a formulation to complex the active drug such that the concentration of the free active drug is reduced below a tolerable threshold. In addition, an effective amount of a viscosity-enhancing agent is incorporated into said formulation such that the bioavailability of said drug is high enough to be therapeutically effective, wherein the cyclodextrin or cyclodextrin derivative is not required to solubilize or stabilize the active drug.

Another aspect of this invention relates to a topical ophthalmic formulation comprising a therapeutically active amount of an ophthalmic drug, an effective amount of a cyclodextrin or cyclodextrin derivative to complex the active drug such that the concentration of the free active drug is lowered sufficiently to significantly reduce irritating side effects, and an effective amount of a viscosity increasing agent such that the bioavailability of said active drug is high enough to be therapeutically effective, wherein the cyclodextrin or cyclodextrin derivative is not required to solubilize or stabilize the active drug.

Another aspect of this invention relates to a method of reducing a side effect associated with a drug administered topically to a patient's eye comprising:

(a) providing a solution of said drug in a therapeutically effective amount, which therapeutically effective amount causes said side effect;

(b) complexing a portion of said drug in said solution with a cyclodextrin or cyclodextrin derivative to lower the free active concentration such that the severity of said side effect is reduced; and (c) incorporating an effective amount of a viscosity increasing agent into said solution to increase the contact time of said solution at the point of administration to the eye of said patient such that the drug is delivered more effectively, whereby the complexed portion of the drug is released over time at a rate insufficient to cause said side effect.

Another aspect of this invention relates to a topical ophthalmic composition prepared by a process comprising (a) providing a solution of a stable and soluble drug in a therapeutically effective amount, which therapeutically effective amount causes a side effect;

(b) complexing a portion of said drug in said solution with a cyclodextrin or cyclodextrin derivative to lower the free active concentration such that the severity of said side effect is reduced; and (c) incorporating an effective amount of a viscosity increasing agent into said solution to increase the contact time of said solution at the point of administration to the eye of said patient such that the drug is delivered more effectively.

BRIEF DESCRIPTION OF THE DRAWING FIGURES

FIG. 1 is a bar graph comparing the peak concentration and area under the curve (total bioavailability) of bimatoprost in the aqueous humor of rabbits after topical administration of formulations 1–3 containing bimatoprost.

DETAILED DESCRIPTION OF THE INVENTION

This invention relates to a method of reducing an irritating or adverse side effect associated with the topical ophthalmic use of an active ophthalmic drug. The attenuation of the irritating side effect is accomplished by incorporating an effective amount of a cyclodextrin or cyclodextrin derivative into the formulation containing said drug to complex the active drug such that the concentration of the free active drug is reduced below a tolerable threshold. To compensate for the loss of bioavailability associated with the use of a cyclodextrin or cyclodextrin derivative, an effective amount of a viscosity-enhancing agent is used in the formulation with said drug, such that the bioavailability of said drug is high enough to be therapeutically effective. Unlike the related art, the cyclodextrin or cyclodextrin derivative is not required to solubilize or stabilize the active drug, meaning the drug is soluble and stable in the formulation in the absence of the cyclodextrin or cyclodextrin derivative.

The term "complex" related to an active drug has the meaning generally understood by those skilled in the art, and refers to noncovalent binding of the active drug to a cyclodextrin or cyclodextrin derivative such that significant changes in the physical, chemical, biological, pharmacokinetic, or spectroscopic properties of the active drug can be observed. The terms "complex" and "complexed active drug" should be interpreted broadly, and although the complexed active drug may be in the form of an inclusion compound, this does not necessarily have to be the case. The term "free active drug" refers to that portion of the active drug which is not complexed with the cyclodextrin or cyclodextrin derivative.

Another embodiment of this invention relates to a topical ophthalmic formulation comprising a therapeutically active amount of an ophthalmic drug, an effective amount of a cyclodextrin or cyclodextrin, and an effective amount of a viscosity-enhancing agent. Unlike the related art, the cyclodextrin or cyclodextrin derivative is not required to solubilize or stabilize the active drug. This means that the drug does not precipitate or chemically degrade in the formulation for two years when stored at about 15° C. to about 30° C., and three years when stored at 4° C. in the absence of a cyclodextrin or cyclodextrin derivative. The concentration of the cyclodextrin or cyclodextrin derivative is high enough to reduce the concentration of the free active drug so that the adverse irritating side effects are reduced to an acceptable level. An effective amount of a viscosity-enhancing agent is the quantity required to compensate for the reduced free drug concentration in the tears accompanying complexation of the active drug. By prolonging the precorneal residence time, this viscosity agent effectively restores the desired therapeutic effect of the active ingredient.

While not intending to be bound in any way by theory, the principles of this invention can be understood by considering the dynamic equilibrium between the complexed active drug and the free active drug. It is believed that the irritating side effects of an active drug are determined by the concentration of free active on the ocular surface. It is also believed that the cyclodextrin-drug complex itself cannot cross cell membranes and be transported into the ocular tissues. However, the bioavailability of the drug is affected by both the concentration of the free active drug in the formulation and the dissociation rate between the complexed and the free active drug. For the purpose of this discussion, we define the term "dissociation rate" as the rate at which the cyclodextrin complex releases free active drug on the ocular surface. This release rate is not expected to be the same as occurs upon simple dilution of the cyclodextrin-drug complex in saline because lipid and/or protein components of the tear film may compete with and displace active drug from the cyclodextrin complex.

We have unexpectedly found that cyclodextrin and cyclodextrin derivatives can be used to complex the active drug such that the concentration of an active drug is low enough to reduce or eliminate the irritating side effects, but the dissociation rate is high enough that adequate bioavailability of the drug is achieved. In other words, as the free drug is consumed by transport into the ocular tissues, more drug is released from the cyclodextrin complex. This release must occur at a high enough rate that said drug is therapeutically available while the topical composition is in contact with the ocular surface, before the composition is flushed from the surface by tears, or removed by blinking, etc. As mentioned previously, although the dissociation rate is great enough for some of the originally complexed drug to become therapeutically available when the free active drug is consumed, some loss of bioavailability is still observed due to the use of the cyclodextrin or cyclodextrin derivative. This loss of bioavailability is countered by optimizing the cyclodextrin-drug ratio and by the use of an appropriate viscosity-enhancing agent. While not desiring to be bound in any way by theory, it is believed that the viscosity-enhancing agent increases the amount of time that the topical ophthalmic formulation can adhere to the eye, thus allowing more of the complexed drug to be released for therapeutic use.

In a preferred embodiment of this invention the concentration of the cyclodextrin or cyclodextrin derivative is between about 0.01% and about 10%. In a more preferred embodiment of this invention the concentration of the cyclodextrin or cyclodextrin derivative is between about 0.05% and about 5%. In the most preferred embodiment of this invention the concentration of the cyclodextrin or cyclodextrin derivative is between about 0.05 and about 1.1%.

While not intending to narrow the scope of the invention in any way, in some situations it may be desirable to optimize the type of cyclodextrin or cyclodextrin derivative used in an effort to optimize the equilibrium between the complexed and free active drug as well as the dissociation rate of the free active drug from the cyclodextrin-drug complex. Doing this may be effective in making more of the active drug available for therapeutic uses while keeping the concentration of the free active drug low enough to avoid unacceptable levels of irritating side effects. This is done by varying the cyclodextrin or cyclodextrin derivative used in a formulation and testing the properties of the formulation prepared by the methods to be described herein. In preferred embodiments of this invention, the cyclodextrin or cyclodextrin derivative is 2-hydroxypropyl β-cyclodextrin, 2-hydroxypropyl γ-cyclodextrin, or native γ-cyclodextrin.

In a preferred embodiment of this invention, the amount or type of cyclodextrin or cyclodextrin derivative is adjusted so that free active drug comprises between about 8% and about 90% of the total active drug. More preferably, the free active drug comprises between about 8% and about 75% of the total active drug. Most preferably, the free active drug comprises between about 8% and about 25% of the total active drug.

This invention relates to active drugs used in topical ophthalmic formulations. While not intending to limit the scope of the invention in any way, typical examples of drugs used in topical ophthalmic formulations are prostaglandins, β-adrenoreceptor antagonists and $α_2$-adrenoreceptor agonists, antihistamines, anti-infective agents, and anti-inflammatory agents. In a preferred embodiment of this invention, the active drug is a prostaglandin. Prostaglandins can be described as derivatives of prostanoic acid which have the following structural formula:

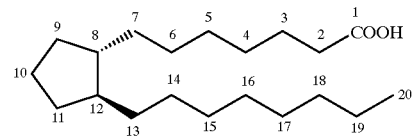

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$(PGE$_1$), prostaglandin $E_2$ (PGE$_2$)], and on the configuration of the substituents on the alicyclic ring indicated by α or β [e.g. prostaglandin $F_{2α}$ (PGF$_{2β}$)].

Prostaglandins were earlier regarded as potent ocular hypertensives, however, evidence accumulated in the last two decades shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

In another preferred embodiment of this invention, the active drug is a prostamide. Prostamides are related to prostaglandins in that the carboxylic acid or ester at $C_1$ is substituted with an amide functional group. For the purposes of this invention, the term amide has the meaning generally understood by organic chemists. Prostamides are prepared by methods generally known in the art, and also by the methods described in U.S. Pat. No. 5,688,819, incorporated herein by reference. In the most preferred embodiment of this invention, the active drug is bimatoprost, which is marketed under the tradename Lumigan® by Allergan, Inc.

In the preferred embodiment of this invention the concentration of bimaprost in an ophthalmic formulation is between about 0.003% and about 0.1%, more preferably the concentration is between about 0.01% and about 0.05%, and most preferably the concentration is about 0.03%.

The term "irritating side effect" refers to any side effect or adverse event characterized by irritation on or near the surface of the eye and surrounding tissues. Such adverse events include, but are not limited to, stinging, ocular dryness, foreign body sensation, and ocular itchiness. In a preferred embodiment of this invention, the irritating side effect being reduced is ocular surface hyperemia. In embodiments of this invention where the hyperemia associated with the use of bimatoprost is reduced, it is preferable that the concentration of free (uncomplexed) bimatoprost is less than 0.02%.

As mentioned, a viscosity-enhancing agent is used in this invention to improve the bioavailability of the active drug. While not intending to limit the scope of the invention, we have found that it is preferable for the viscosity of the formulation to be between about 30 centipoise and about 100 centipoise. We have also found that the preferred concentration of the viscosity increasing agent is between about 0.1% and about 3%, more preferably the concentration of the viscosity agent is about 1%. The viscosity-enhancing agent may comprise a polymer containing hydrophilic groups such as monosaccharides, polysaccharides, ethylene oxide groups, hydroxyl groups, carboxylic acids or other charged functional groups. While not intending to limit the scope of the invention, some examples of viscosity-enhancing agents useful in this invention are sodium carboxymethylcellulose, hydroxypropylmethylcellulose, povidone, polyvinyl alcohol, and polyethylene glycol. Preferably, the viscosity-enhancing agent is sodium carboxymethylcellulose or hydroxypropylmethylcellulose. Most preferably, the viscosity-enhancing agent is sodium carboxymethylcellulose. Particularly useful grades of sodium carboxymethylcellulose are sold under the trade name Aqualon® by Hercules, with low molecular weights of 100,000–900,000, and about 0.65–0.95 hydroxyl groups on each glucose unit substituted with carboxymethylether groups.

In another preferred embodiment, the topical ophthalmic formulation of this invention further comprises an effective amount of buffer necessary to maintain the pH at about 7.3, one or more tonicity agents, and a preservative.

Buffering agents used are those known to those skilled in the art, and, while not intending to be limiting, some examples are acetate, borate, carbonate, citrate, and phosphate buffers. In the most preferred embodiment of this invention, the buffer comprises borate.

The tonicity agents are used to adjust the composition of the formulation to the desired isotonic range. Tonicity agents are known to those skilled in the ophthalmic art, and, while not intending to be limiting, some examples include glycerin, mannitol, sorbitol, sodium chloride, and other electrolytes. In the preferred embodiment of this invention, the tonicity agent is sodium chloride.

In another preferred embodiment of this invention, a preservative is used. Preservatives are used to prevent bacterial contamination in multiple-use ophthalmic preparations, and, while not intending to be limiting, examples include benzalkonium chloride, stabilized oxychloro complexes (otherwise known as Purite®™?), phenylmercuric acetate, chlorobutanol, benzyl alcohol, parabens, and thimerosal. In a preferred embodiment of this invention, the preservative is Purite®, manufactured by Bio-Cide International, Inc, in Norman, Okla. Purite is an aqueous solution that has sufficient oxychloro complex to generate 2.1–2.3% chlorine dioxide. Purite (oxychloro complex) solution comprises of an equilibrium mixture of oxychloro species, predominantly chlorite ($NaClO_2$, at 99.5%), chlorate ($NaClO_3$, ~0.5%) and traces of chlorine dioxide ($ClO_2$).

A person skilled in the art will recognize that there are many ways in which the preferences described above can be combined to form unique embodiments. Any combination of the preferences mentioned herein which would be obvious to those of ordinary skill in the art are considered to be separate embodiments which fall within the scope of this invention.

In addition to the considerations above, optimization of the formulation involves choosing both the type and concentration of the buffering system, the tonicity agent, and the preservative. In the current invention, optimization provides for more than just enhanced patient comfort. Any significant stinging, burning, or irritation upon instillation of the prescribed dose will elicit tear flow which in turn will tend to flush the cyclodextrin-drug complex from the ocular surface before adequate drug transport into the ocular tissues has occurred. Once the determinations of the concentration and type of cyclodextrin or cyclodextrin derivative and the viscosity-enhancing agent are made, optimization of the remaining ingredients of the formulation are well within the ability of a person of ordinary skill in the art.

The best mode of making and using the present invention are described in the following examples. These examples are given only to provide direction and guidance in how to make and use the invention, and are not intended to limit the scope of the invention in any way.

EXAMPLE 1

Formulation 1 was prepared as follows using the amounts shown below. All steps in the procedure of this example and the other examples were carried out at room temperature. Purified water (~80% of batch size) was measured into an appropriately sized mixing container. Vigorous mixing was started using an overhead mixer (Rotosolver) to form a strong vortex. The following ingredients were added into the vortex in order shown, allowing each to dissolve before the next addition: sodium chloride, sodium phosphate, citric acid and benzalkonium chloride. The pH was checked and adjusted as needed with dilute hydrochloric acid or sodium hydroxide solution to pH 7.3. Bimatoprost was added during vigorous mixing and mixing was continued for 30–35 minutes so that the solution was clear. Purifed water was added to correct the final volume. The solution was sterilized by passage through a sterile filtration apparatus fitted with a 0.2 μm membrane.

| Formulation 1 | Grams/100 mL |
|---|---|
| Bimatoprost [mw = 415] | 0.03 |
| Sodium chloride | 0.83 |
| Sodium phosphate | 0.268 |
| Citric acid | 0.014 |
| Benzalkonium chloride | 0.005 |

EXAMPLE 2

Formulation 2 was prepared as follows using the amounts shown below. All steps in the procedure were carried out at room temperature.

Sodium Carboxymethylcellulose (Part I)

Purified water was measured (~50% of batch size) into an appropriately sized mixing container and vigorous mixing was started using an overhead mixer (Rotosolver) such that a strong vortex formed. Sodium carboxymethylcellulose (purchased from Aqualon, a division of Hercules) was added to the vortex at a rapid rate, and the mixture was vigorously mixed for 30–35 minutes. Part I was quantitatively transferred to a Pyrex bottle using purified water as a rinse. The final volume was about 60% of batch size. The bottle was capped, and Part I was sterilized by autoclaving for 50 minutes at 121° C., then cooled to room temperature.

Salt and Drug Solution (Part II)

Purified water (~35% of batch size) was measured into an appropriately sized mixing container. Vigorous mixing was started using an overhead mixer (Rotosolver) to form strong vortex, and the following ingredients were added into the vortex in order shown, allowing each to dissolve before the next addition: boric acid, sodium borate, sodium chloride, potassium chloride, magnesium chloride, calcium chloride, bimatoprost, and 2% Purite® solution.

Filtration Procedure

Part II was filtered into Part I using a sterile filtration apparatus with a 0.2 μm membrane, and the container was rinsed with purified water and filtered into Part I. Additional purified water (by weight) was filtered into Part I to correct final volume.

| Formulation 2 | Grams/100 mL |
|---|---|
| Bimatoprost [mw = 415] | 0.03 |
| Carboxymethylcellulose | 1.00 |
| Boric acid | 0.60 |
| Sodium borate | 0.045 |
| Sodium chloride | 0.34 |
| Potassium chloride | 0.14 |
| Calcium chloride | 0.006 |
| Magnesium chloride | 0.006 |
| Purite | 0.010 |

Formulations 1–2 yielded clear solutions, demonstrating that the cyclodextrin derivatives are not required to solubilize the bimatoprost.

EXAMPLE 3

Formulation 3 was prepared in the same manner as formulation 2, except that ingredients added to the vortex in Part II are made with the addition of 2-hydroxypropyl β-cyclodextrin (purchased from Wacker Biochem Corp., Adrian Mich., under the tradename Cavasol W7 HP®) in the following order: boric acid, sodium borate, sodium chloride, potassium chloride, magnesium chloride, calcium chloride, 2-hydroxypropyl β-cyclodextrin, bimatoprost, and 2% Purite solution.

| Formulation 3 | Grams/100 mL |
|---|---|
| Bimatoprost [mw = 415] | 0.03 |
| 2-Hydroxypropyl β-cyclodextrin [mw ≈ 1400] | 1.011 |
| Carboxymethylcellulose | 1.00 |
| Boric acid | 0.60 |
| Sodium borate | 0.045 |
| Sodium chloride | 0.34 |
| Potassium chloride | 0.14 |
| Calcium chloride | 0.006 |
| Magnesium chloride | 0.006 |
| Purite | 0.010 |

Notes
1-Hydroxypropyl β-cyclodextrin is added to about ten-fold molar excess relative to bimatoprost.

EXAMPLE 4

The association constant between an active drug and a cyclodextrin or cyclodextrin derivative is used to quantify the equilibrium association reaction depicted in equation 1, $$D + CD = D \ldots CD \quad (1)$$

where D represents the active drug, CD represents the cyclodextrin or cyclodextrin derivative, and D . . . CD represents the associated complex of the two. The association constant, K, defines the relationship between the molar concentration of the active drug, [D], the molar concentration of the cyclodextrin or cyclodextrin derivative, [CD], and the molar concentration of the complex, [D . . . CD], according to equation 2.

$$K = \frac{[D \ldots CD]}{[D][CD]} \quad (2)$$

The association constant between the bimatoprost and four cyclodextrin or cyclodextrin derivatives was determined by running phase-solubility analysis. A series of small glass bottles was set up, each fitted with a screw cap and a magnetic stir bar with increasing concentrations of cyclodextrin or cyclodextrin derivative dissolved in a fixed volume (e.g., 10 mL) of aqueous vehicle (e.g., the formulation minus the drug and the cyclodextrin or cyclodextrin derivative). Enough of the active drug was added to each bottle to exceed its aqueous solubility by about a factor of 10. Bottles were then capped and the suspensions were stirred for a week at room temperature to ensure equilibrium. Undissolved drug was removed by centrifugation, followed by filtration through a 0.45 μm filter membrane to obtain a clear solution, free of drug in suspension. The concentration of the solubilized drug in each filtrate sample was determined and drug solubility (y-axis) was plotted against the concentration of the cyclodextrin or cyclodextrin derivative (x-axis). A linear fit of the data was made using least-squares regression to a linear to equation (3).

$$y = (\text{slope})x + b \quad (4)$$

The association constant for a 1:1 complex (K) was determined by equation (5)

$$K = \text{slope}/S_0(1-\text{slope}) \quad (5)$$

where $S_0$ is the maximum solubility of the active drug in the formulation in the absence of the cyclodextrin or cyclodextrin derivative. In principle, $S_0$ is equivalent to the y intercept (b) of the fitted line, however, in most cases it can more accurately be determined by direct measurement of the solubility rather than indirectly from the fit of data.

For bimatoprost, experimentally determined molar association constants are shown in Table 1.

TABLE I

Molar Association Constants for Bimatoprost

| Cyclodextrin Type | Association Constant ($M^{-1}$) |
|---|---|
| 2-Hydroxypropyl β-cyclodextrin (mw ≈ 1400) | ≈1913 |
| Sulfobutyl ether β-cyclodextrin (mw ≈ 2160) | ≈1464 |
| γ-cyclodextrin (mw ≈ 1297) | ≈439 |
| 2-Hydroxypropyl γ-cyclodextrin (mw ≈ 1576) | ≈201 |

Pharmacokinetic studies were carried out using formulations 1–3. A single 20 μL drop of formulation 1, 2 or 3, was placed on the eyes of an albino rabbit. A total of two rabbits at each of five time points were tested for each formulation. Tissue samples were removed at time intervals from 0.5 to 6 hours, and the concentration of bimatoprost in aqueous humor determined by HPLC analysis. The results, shown in FIG. 1, are a good model for bioavailability in human subjects being treated with bimatoprost for glaucoma.

Turning to FIG. 1, the aqueous humor concentration in the rabbits treated with each of the three formulations is shown. It should be emphasized that the concentration of the active drug in each formulation is the same, and that all three formulations were clear solutions. In formulations 1 and 2, 100% of the active drug is in the free (uncomplexed) form since no cyclodextrin or cyclodextrin derivative is present. In formulation 3, the free active drug was calculated to be only 8% of the total active drug using equation 2 and Table 1. In other words, 92% of the active drug in formulation 3 is in the complexed form. Comparison of the results for formulation 2 and 3 reflect the effect that the cyclodextrin has upon the bioavailability of the drug. For both the peak concentration and the total area under the curve, the activity of formulation 3 is about 25% that of formulation 2, while formulation 3 contains only 8% free drug where 100% of the drug in formulation 2 is in the free form. Although the relationship may not necessarily be linear, one would expect that by reducing the amount of cyclodextrin used, the bioavailability of the drug could be increased while still keeping the concentration of the free drug significantly below 100% of the total active drug. Alternatively, varying the cyclodextrin will modify the binding equilibrium or the dissociation rate, which may favor increased bioavailability. For example, using γ-cyclodextrin instead of β-cyclodextrin would provide a looser fit for the active drug because the γ-cyclodextrin has a larger cavity arising from the extra glucopyranose unit in the ring, as demonstrated by γ-cyclodextrin's lower association constant in Table 1. In addition to modifying the cyclodextrin or cyclodextrin derivative or adjusting its concentration to modify the bioavailability, the bioavailability can be increased by using a viscosity-enhancing agent without increasing the concentration of the free active drug. If the reasonable assumption is made that the differences between the salts, buffers, and preservatives of formula 1 and formula 2 have a negligible effect on bioavailability, comparison of the results for formulation 1, which contains no viscosity-enhancing agent, with formulation 2 which does contain the viscosity-enhancing agent shows that viscosity-enhancing agent significantly improves the bioavailability of the drug. Comparison of the formulation 1 with formulation 3 demonstrates what the combination of a cyclodextrin or cyclodextrin derivative with a viscosity-enhancing agent can be used to accomplish. Thus, although formulation 3 only contains 8% of the free drug, which would result in a significant reduction in irritating side effects, the bioavailability of bimatoprost in formulation 3 is significantly higher than 8% of that of formulation 1. In this case, the peak concentration of formulation 3 is 75% and the total bioavailability is 40% of that of formulation 1. However, with a few routine experiments where either the concentration of the viscosity-enhancing agent or the cyclodextrin concentration is varied, the bioavailability of bimatoprost could reasonably be expected to match or exceed that of formulation 1.

Clinical trials have shown that 0.02% bimatoprost shows little hyperemia, but also loses efficacy. Therefore, when the concentration of free bimatoprost is around or below 25–75%, the hyperemia should be reduced significantly. On the other hand, in formulation 3 only 8% of the bimatoprost is in the free form, so the amount of free active drug could be increased by a factor of 3–9 before hyperemia should become significant, leaving plenty of room to improve the bioavailability of the drug while still exhibiting significantly reduced hyperemia.

Formulating a Water-Soluble Drug to Reduce Irritating Side Effects

EXAMPLE 5

As a starting point, a formulation of 0.03% bimatoprost which is expected to have 0.019% free (uncomplexed) bimatoprost is prepared using 2-hydroxypropyl γ-cyclodextrin. Since a formulation containing no cyclodextrin or cyclodextrin derivative and 0.02% bimatoprost has little hyperemia, a formulation containing 0.019% free bimatoprost in and 0.011% complexed bimatoprost will have significantly reduced hyperemia compared to a 0.03% bimatoprost formulation containing no cyclodextrin or cyclodextrin derivative. The quantity of hydroxypropyl γ-cyclodextrin required in the formulation to obtain 0.019% free bimatoprost and 0.011% complexed bimatoprost is calculated from equation 2 and Table 1. In a situation such as this where the desired ratio of complexed to free active drug is known, Equation 2 can be simplified and rearranged to equation 6

$$[CD] = R/K \quad (6)$$

where R is the ratio of the complexed to the uncomplexed active drug (R=[D . . . CD]/[D]). The total cyclodextrin or cyclodextrin derivative concentration in the formulation is then [CD]+[D . . . CD]. Using this relationship, one obtains a concentration of about 0.5 g/L for 2-hydroxypropyl γ-cyclodextrin as a starting point for formulation of a product containing 0.03% bimatoprost for reduced hyperemia.

Formulation 4 is prepared in the same manner as formulation 3, with the exception that 2-hydroxypropyl γ-cyclodextrin (purchased from Wacker Biochem Corp., Adrian Mich. under the tradename Cavasol W8 HP®) at the given concentration was used in place of 2-hydroxypropyl γ-cyclodextrin. If the viscosity of the formulation is not in the 50 to 100 cps range, it is adjusted by reformulating with an adjusted quantity of sodium carboxymethylcellulose to obtain an acceptable viscosity.

| Formulation 4 | Grams/100 mL |
| --- | --- |
| Bimatoprost [mw = 415] | 0.03 |
| 2-Hydroxypropyl γ-cyclodextrin [mw ≈ 1576] | 0.50 |
| Carboxymethylcellulose | 1.00 |
| Boric acid | 0.60 |
| Sodium borate | 0.045 |
| Sodium chloride | 0.34 |
| Potassium chloride | 0.14 |
| Calcium chloride | 0.006 |
| Magnesium chloride | 0.006 |
| Purite | 0.010 |

The formulation is then tested as described in Example 3, and the concentration of hydroxypropyl γ-cyclodextrin is adjusted according to the results if necessary.

EXAMPLE 6

The concentration of γ-cyclodextrin used as a starting point for the Formulation 5 is determined as described in Example 5. Formulation 5 is then prepared in the same manner as formulation 4, with the exception that γ-cyclodextrin (purchased from Wacker Biochem Corp., Adrian Mich. under the tradename Cavasol W8®) at the given concentration is used in place of 2-hydroxypropyl γ-cyclodextrin.

| Formulation 5 | Grams/100 mL |
| --- | --- |
| Bimatoprost | 0.03 |
| γ-cyclodextrin [mw ≈ 1297] | 0.21 |
| Carboxymethylcellulose | 1.00 |
| Boric acid | 0.60 |
| Sodium borate | 0.045 |
| Sodium chloride | 0.34 |
| Potassium chloride | 0.14 |
| Calcium chloride | 0.006 |
| Magnesium chloride | 0.006 |
| Purite | 0.010 |

The formulation is then tested as described in Example 3, and the concentration of γ-cyclodextrin is adjusted according to the results if necessary.

EXAMPLE 7

Formulation 6 is prepared and tested in an analogous manner to those described in Examples 5–6.

| Formulation 6 | Grams/100 mL |
| --- | --- |
| Bimatoprost | 0.03 |
| 2-Hydroxypropyl β-cyclodextrin [mw ≈ 1400] | 0.08 |
| Carboxymethylcellulose | 1.00 |
| Boric acid | 0.60 |
| Sodium borate | 0.045 |
| Sodium chloride | 0.34 |
| Potassium chloride | 0.14 |
| Calcium chloride | 0.006 |
| Magnesium chloride | 0.006 |
| Purite | 0.010 |

EXAMPLE 7

A formulation prepared according to Example 5 is administered to glaucoma patients who experience reduced intraocular pressure similar to that observed in patients who are treated with formulation 1. However, significantly reduced hyperemia is observed in the patients treated with the formulation relative to those treated with formulation 1.

EXAMPLE 9

A formulation prepared according to example 6 is administered to glaucoma patients who experience reduced intraocular pressure similar to that observed in patients who are treated with formulation 1. However, significantly reduced hyperemia is observed in the patients treated with the formulation relative to those treated with formulation 1.

What is claimed is:

1. A topical ophthalmic formulation comprising bimatoprost at a concentration of from 0.003% and 0.1%, an effective amount of a cyclodextrin derivative, and an effective amount of a viscosity increasing agent.

2. The topical ophthalmic formulation of claim 1 which further comprises an effective amount of buffer necessary to maintain the pH at about 7.3, one or more tonicity agents, and a preservative.

3. The topical ophthalmic formulation of claim 2 wherein the buffer comprises borate and the preservative is stabilized oxychloro complexes.

4. The topical ophthalmic formulation of claim 1 wherein the concentration of bimatoprost is between about 0.01% and about 0.05%.

5. The topical ophthalmic formulation of claim 1 wherein the concentration of bimatoprost is about 0.03%.

6. The topical ophthalmic formulation of claim 1 wherein the concentration of free bimatoprost is less than about 0.02%.

7. The topical ophthalmic formulation of claim 1 wherein the cyclodextrin or cyclodextrin derivative is 2-hydroxypropyl β-cyclodextrin, 2-hydroxypropyl γ-cyclodextrin, or γ-cyclodextrin.

8. The topical ophthalmic formulation of claim 1 wherein the concentration of the cyclodextrin or cyclodextrin derivative is between about 0.1% and about 1.1%.

9. The topical ophthalmic formulation of claim 1 wherein the viscosity agent is sodium carboxymethylcellulose or hydroxypropylmethylcellulose.

10. The topical ophthalmic formulation of claim 1 wherein the viscosity agent is sodium carboxymethylcellulose.

11. The topical ophthalmic formulation of claim 10 wherein the concentration of bimatoprost is 0.03%, which further comprises about 0.6% boric acid, about 0.045% sodium borate, about 0.34% sodium chloride, about 0.14% potassium chloride, about 0.006% calcium chloride, about 0.006% magnesium chloride, and about 0.01% Purite®.

12. The topical ophthalmic formulation of claim 1 wherein the free active drug comprises between about 8% and about 90% of the active drug.

13. The topical ophthalmic formulation of claim 1 wherein the free active drug comprises between about 8% and about 75% of the active drug.

14. The topical ophthalmic formulation of claim 1 wherein the free active drug comprises between about 8% and about 25% of the active drug.

* * * * *